United States Patent
Beymer et al.

(10) Patent No.: US 10,522,248 B2
(45) Date of Patent: Dec. 31, 2019

(54) AUTOMATIC CREATION OF IMAGING STORY BOARDS FROM MEDICAL IMAGING STUDIES

(71) Applicant: International Business Machines Corporation, Armonk, NY (US)

(72) Inventors: David J. Beymer, San Jose, CA (US); Ehsan Dehghan Marvast, Palo Alto, CA (US); Ahmed El Harouni, San Jose, CA (US); Yaniv Gur, San Jose, CA (US); Satyananda Kashyap, San Jose, CA (US); Mehdi Moradi, San Jose, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 180 days.

(21) Appl. No.: 15/855,611

(22) Filed: Dec. 27, 2017

(65) Prior Publication Data

US 2019/0198157 A1 Jun. 27, 2019

(51) Int. Cl.
*G06K 9/00* (2006.01)
*G16H 30/40* (2018.01)
(Continued)

(52) U.S. Cl.
CPC .............. *G16H 30/40* (2018.01); *G06F 16/51* (2019.01); *G06F 16/5866* (2019.01);
(Continued)

(58) Field of Classification Search
CPC ........ G16H 30/40; G16H 10/60; G06F 16/51; G06F 16/5866; G06K 9/4671;
(Continued)

(56) References Cited

U.S. PATENT DOCUMENTS 6,006,191 A 12/1999 DiRienzo
8,744,149 B2 * 6/2014 Nakamura ............ G06F 19/321
382/128
(Continued)

OTHER PUBLICATIONS

List of IBM Patents or Patent Applications Treated as Related, Mar. 8, 2018, 2 pages.
(Continued)

*Primary Examiner* — Shefali D Goradia
(74) *Attorney, Agent, or Firm* — Stephen R. Tkacs; Stephen J. Walder, Jr.; William J. Stock

(57) ABSTRACT

A mechanism is provided in a data processing system comprising a processor and a memory, the memory comprising instructions that are executed by the processor to specifically configure the processor to implement a medical imaging story board creation engine. The medical imaging story board creation engine executing in the data processing system receives a patient data structure comprising a medical imaging study comprising a plurality of electronic medical images. The medical imaging story board creation engine analyzes the patient data structure to determine a modality of the medical imaging study. The medical imaging story board creation engine determines, based on the determined modality of the medical imaging study, for each electronic image in the medical imaging study, at least one of an image mode or viewpoint. The medical imaging story board creation engine performs a saliency feature extraction operation on the electronic medical images in the medical imaging study based on the image mode or viewpoint of each of the electronic medical images. The medical imaging story board creation engine selects a subset of electronic medical images based on results of the saliency feature extraction. The medical imaging story board creation engine generates and outputs a collection of selected electronic medical images
(Continued)

based on the selection of the subset of electronic medical images to form a medical imaging story board.

20 Claims, 6 Drawing Sheets

(51) Int. Cl.

| | | |
|---|---|---|
| *G06T 7/00* | (2017.01) | |
| *G06K 9/46* | (2006.01) | |
| *G06F 16/51* | (2019.01) | |
| *G06F 16/58* | (2019.01) | |
| *A61B 5/055* | (2006.01) | |
| *G16H 10/60* | (2018.01) | |
| *A61B 6/03* | (2006.01) | |
| *A61B 6/00* | (2006.01) | |
| *A61B 8/08* | (2006.01) | |
| *G06N 20/00* | (2019.01) | |
| *G06N 3/04* | (2006.01) | |
| *G06N 3/08* | (2006.01) | |
| *G06N 5/04* | (2006.01) | |
| *A61B 5/00* | (2006.01) | |

(52) U.S. Cl.
CPC .......... *G06K 9/4671* (2013.01); *G06T 7/0012* (2013.01); *A61B 5/0035* (2013.01); *A61B 5/055* (2013.01); *A61B 5/7264* (2013.01); *A61B 6/032* (2013.01); *A61B 6/486* (2013.01); *A61B 6/504* (2013.01); *A61B 6/505* (2013.01); *A61B 8/48* (2013.01); *A61B 8/486* (2013.01); *A61B 8/488* (2013.01); *G06N 3/0454* (2013.01); *G06N 3/08* (2013.01); *G06N 5/041* (2013.01); *G06N 20/00* (2019.01); *G06T 2207/10088* (2013.01); *G06T 2207/30048* (2013.01); *G16H 10/60* (2018.01)

(58) Field of Classification Search
CPC ......... G06T 7/0012; G06T 2207/10088; G06T 2207/30048; G06N 20/00; G06N 3/0454; G06N 3/08; G06N 3/041; A61B 5/0035; A61B 5/055; A61B 5/7264; A61B 6/032; A61B 6/486; A61B 6/504; A61B 6/505; A61B 8/48; A61B 8/486; A61B 8/488
See application file for complete search history.

(56) References Cited

U.S. PATENT DOCUMENTS

| | | | |
|---|---|---|---|
| 9,313,623 B1* | 4/2016 | Ledet | .................. G06F 19/3456 |
| 9,430,828 B2 | 8/2016 | Wu et al. | |
| 2012/0250961 A1* | 10/2012 | Iwasaki | .................. G06F 19/321 |
| | | | 382/128 |
| 2013/0083894 A1* | 4/2013 | Niebler | ................ A61B 6/4441 |
| | | | 378/62 |
| 2014/0043334 A1 | 2/2014 | Noshi | |
| 2014/0063208 A1 | 3/2014 | Fukasawa et al. | |
| 2014/0068653 A1 | 3/2014 | Ohta | |
| 2016/0092656 A1 | 3/2016 | Glaser-Seidnitzer et al. | |
| 2016/0124619 A1 | 5/2016 | McCallum et al. | |
| 2016/0209995 A1 | 7/2016 | Jeon et al. | |
| 2016/0335395 A1 | 11/2016 | Wu et al. | |
| 2017/0038951 A1 | 2/2017 | Reicher et al. | |
| 2017/0039321 A1 | 2/2017 | Reicher et al. | |
| 2017/0039322 A1 | 2/2017 | Reicher et al. | |
| 2017/0046483 A1 | 2/2017 | Reicher et al. | |
| 2017/0083662 A1 | 3/2017 | Florin et al. | |
| 2017/0083665 A1 | 3/2017 | Florin et al. | |
| 2017/0116732 A1 | 4/2017 | Britzen | |
| 2018/0301222 A1* | 10/2018 | Dew, Sr. | ................ G06Q 50/24 |

OTHER PUBLICATIONS

Antani, Sameer et al., "Content-Based Image Retrieval for Large Biomedical Image Archives", MEDINFO 2004: proceedings of the 11th World Congress on Medical Informatics, Aug. 2004, 5 pages.
Sluiters, E.C. , "Timeline visualization of patient information for tumor board presentation", Eindhoven University of Technology, Stan Ackermans Institute, Sep. 15, 2009, 87 pages.
List of IBM Patents or Patent Applications Treated as Related, Dec. 11, 2018, 2 pages.

* cited by examiner

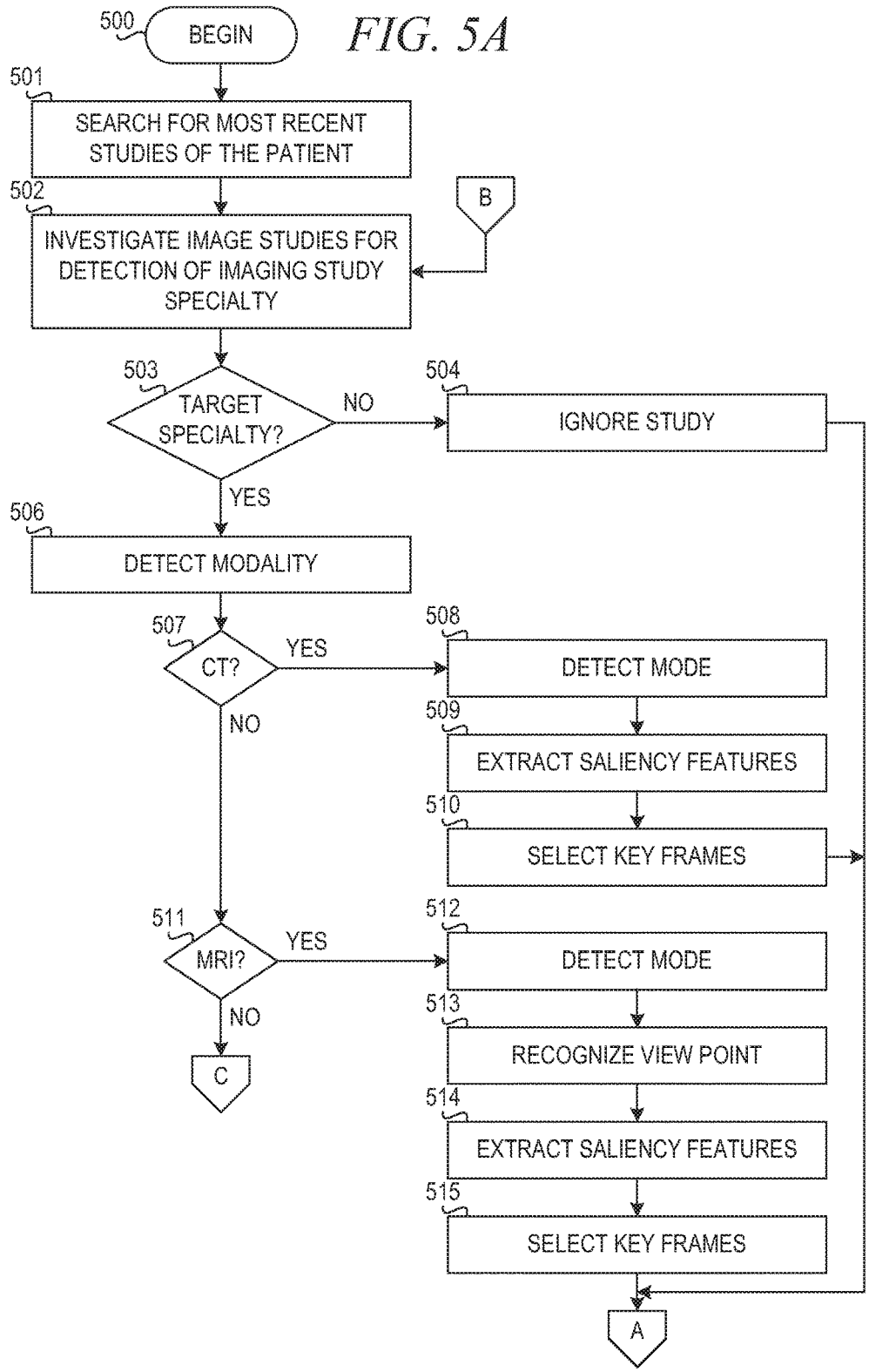

AUTOMATIC CREATION OF IMAGING STORY BOARDS FROM MEDICAL IMAGING STUDIES

BACKGROUND

The present application relates generally to an improved data processing apparatus and method and more specifically to mechanisms for automatic creation of imaging story boards from medical imaging studies.

Medical imaging is the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities. Although imaging of removed organs and tissues can be performed for medical reasons, such procedures are usually considered part of pathology instead of medical imaging.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a medical imaging story board creation engine. The method comprises receiving, by the medical imaging story board creation engine executing in the data processing system, a patient data structure comprising a medical imaging study comprising a plurality of electronic medical images. The method further comprises analyzing, by the medical imaging story board creation engine, the patient data structure to determine a modality of the medical imaging study. The method further comprises determining, by the medical imaging story board creation engine, based on the determined modality of the medical imaging study, for each electronic image in the medical imaging study, at least one of an image mode or viewpoint. The method further comprises performing, by the medical imaging story board creation engine, a saliency feature extraction operation on the electronic medical images in the medical imaging study based on the image mode or viewpoint of each of the electronic medical images. The method further comprises selecting, by the medical imaging story board creation engine, a subset of electronic medical images based on results of the saliency feature extraction. The method further comprises generating and outputting, by the medical imaging story board creation engine, a collection of selected electronic medical images based on the selection of the subset of electronic medical images to form a medical imaging story board.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 5A and 5B present a flowchart of a mechanism for automatic creation of imaging story boards from medical imaging studies in accordance with an illustrative embodiment.

DETAILED DESCRIPTION

Figure 1:
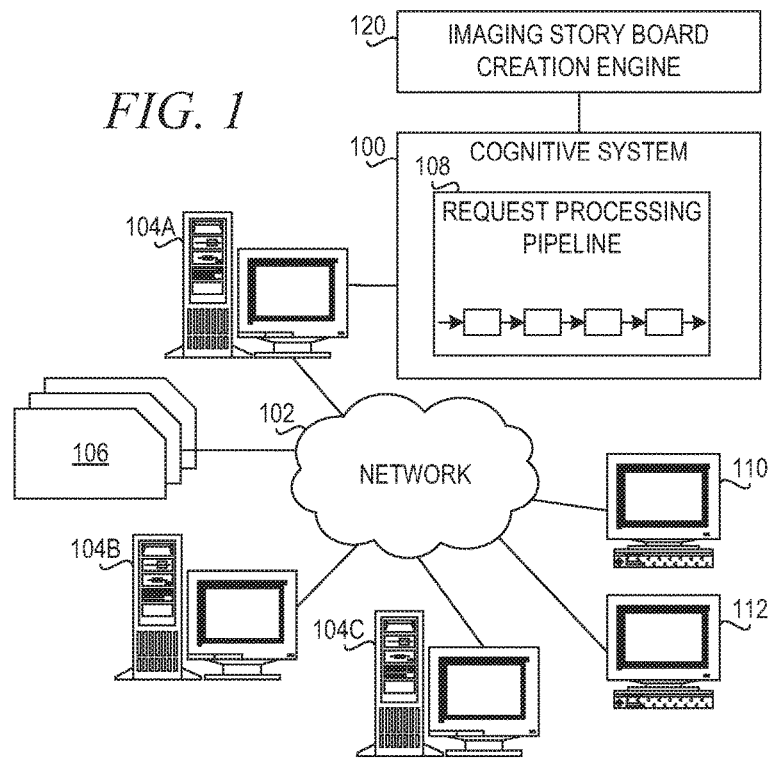
FIG. 1 depicts a schematic diagram of one illustrative embodiment of a cognitive healthcare system in a computer network.

The use of story boards of medical images is a methodology employed to optimize the workflow of a physician by providing a concise summary of imaging studies for quick review. The problem is to determine which images in a medical imaging study, or set of studies, potentially of different modalities (e.g., computerized tomography (CT), magnetic resonance imaging (MRI), angiography, echocardiography, etc.) to include the story board so that the clinician is presented with the most relevant information for making clinical decisions. Imaging studies are tests performed with a variety of techniques that produce pictures of the inside of a patient's body. Imaging tests are performed using sound waves, radioactive particles, magnetic fields, or x-rays that are detected and converted into images after passing through body tissues. Currently, a story board is generated by showing all the available images ordered by the time of acquisition.

The illustrative embodiments provide an automated proactive selection of salient images from one or more imaging studies for inclusion in a story board to be presented to a clinician rather than requiring time consuming manual processes that require the clinician to comb through large size imaging studies to find the salient images.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
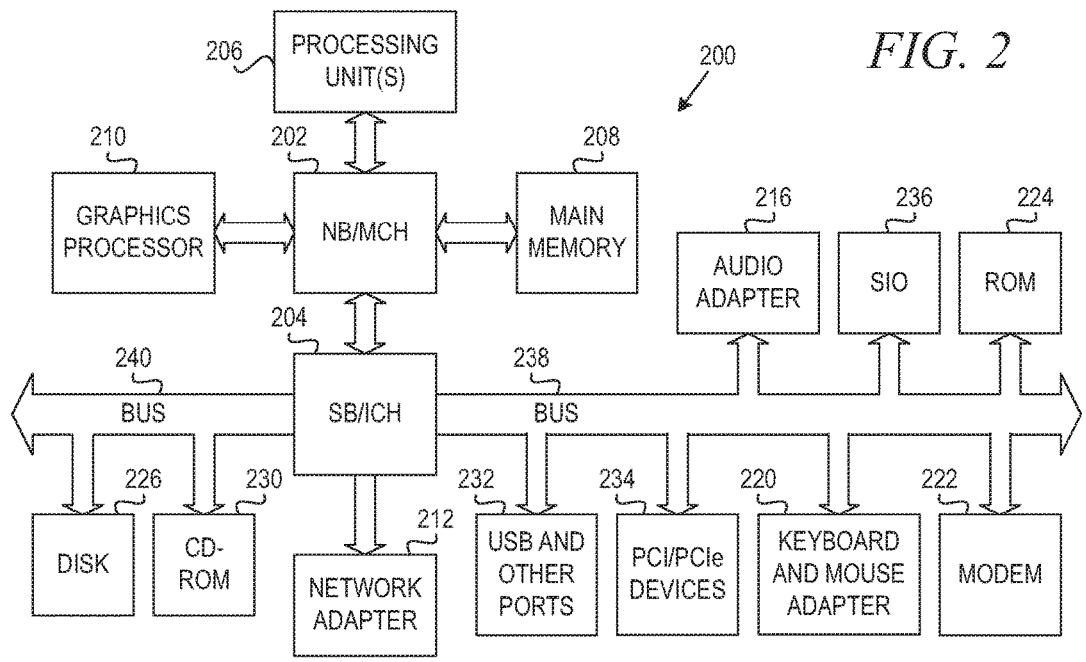
FIG. 2 is a block diagram of an example data processing system in which aspects of the illustrative embodiments are implemented.
Figure 3:
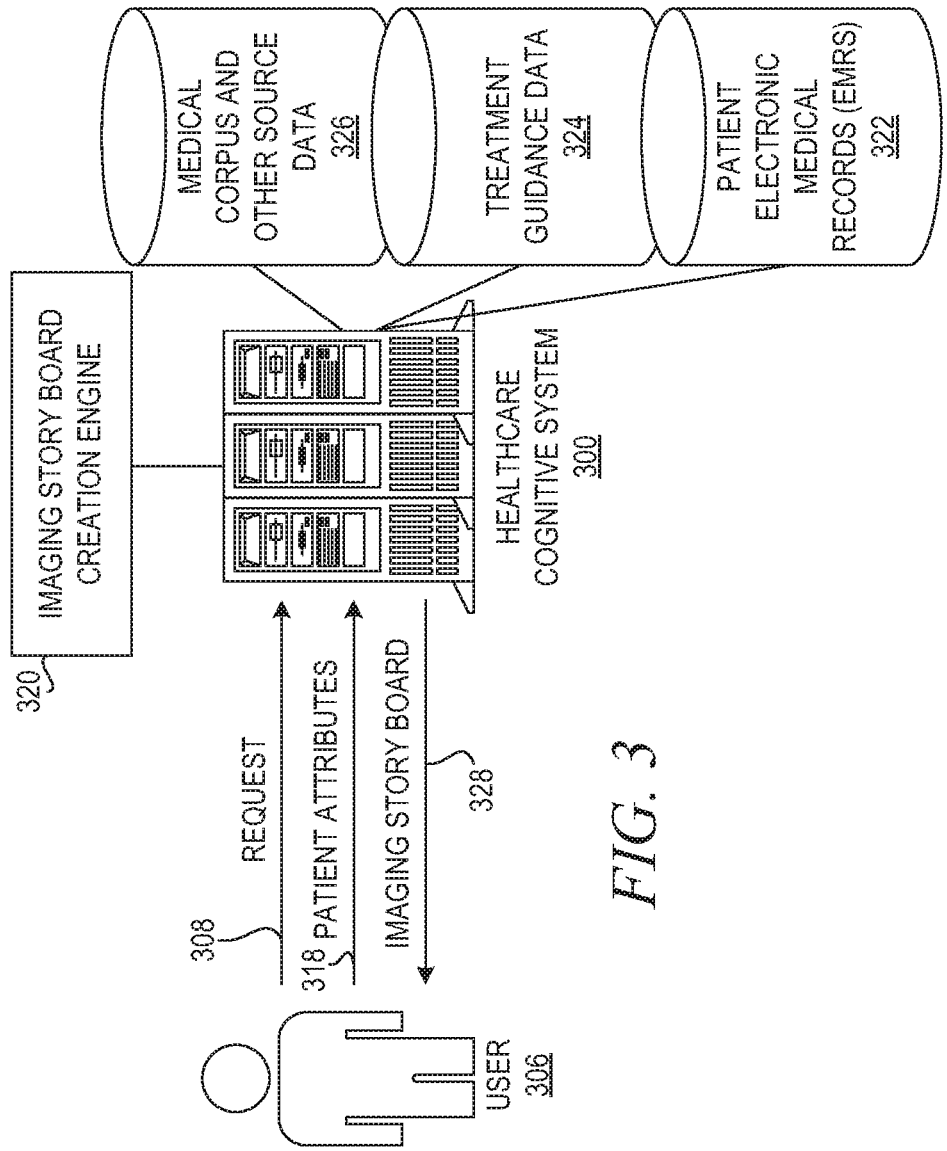
FIG. 3 is an example diagram illustrating an interaction of elements of a healthcare cognitive system in accordance with one illustrative embodiment.

FIGS. 1-3 are directed to describing an example cognitive system for healthcare applications (also referred to herein as a "healthcare cognitive system") which implements a request processing pipeline, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for evaluating the completeness and data quality of electronic medical record data sources.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As will be discussed in greater detail hereafter, the illustrative embodiments may be integrated in, augment, and extend the functionality of the request processing pipeline to include mechanisms of a healthcare cognitive system with regard identifying key images from medical imaging studies based on image analysis and clinical knowledge protocols.

Thus, it is important to first have an understanding of how cognitive systems in a cognitive system implementing a request processing pipeline is implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing an input request based on information obtained from the corpus or corpora of data 106. The pipeline 108 generates responses for the input question or request based on the processing of the input request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input request which it then parses to extract the major features of the request, which in turn are then used to formulate queries that are applied to the corpus or corpora of data 106. Based on the application of the queries to the corpus or corpora of data 106, a set of hypotheses, or candidate responses to the input request, are generated by looking across the corpus or corpora of data 106 for portions of the corpus or corpora of data 106 (hereafter referred to simply as the corpus 106) that have some potential for containing a valuable response to the input response. The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes. Thus, the cognitive system 100 may be a healthcare cognitive system 100 that operates in the medical or healthcare type domains and which may process requests for such healthcare operations via the request processing pipeline 108 input as either structured or unstructured requests, natural language input, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing an image story board creation engine 120, which is described in further detail below.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a medical image story board for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a medical imaging story board 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate imaging story board 328.

Thus, in accordance with the illustrative embodiments herein, the healthcare cognitive system 300 is augmented to include an imaging story board creation engine 320 that selects the most salient images from one or more medical imaging studies for inclusion in a medical imaging story board to be presented to a clinician to assist with making clinical decisions. Given a specialty and/or other criteria for the generation of the story board, imaging story board creation engine 320 receives an imaging study, determines a specialty of the received imaging study, and determines a modality of the imaging study. Based on the specialty of the imaging study, imaging story board creation engine 320 determines whether to keep the imaging study for evaluation in generating the story board or not. For example, if the specialty of the imaging study does not match the specialty for which the story board is being generated, then the imaging study may be discarded. Thereafter, based on the modality of the imaging study, imaging story board creation engine 320 analyzes the images in the imaging study to perform salient feature extraction based on a medical knowledge base. The salient feature extraction may be performed differently based on the particular modality. Based on the salient feature extraction, imaging story board creation engine 320 selects key frames from the imaging study and combines them into a story board, which may be saved and/or presented to the clinician. Moreover, a clinician may specify the important features to look for in order to drive the salient feature extraction and key frame selection.

Figure 4A:
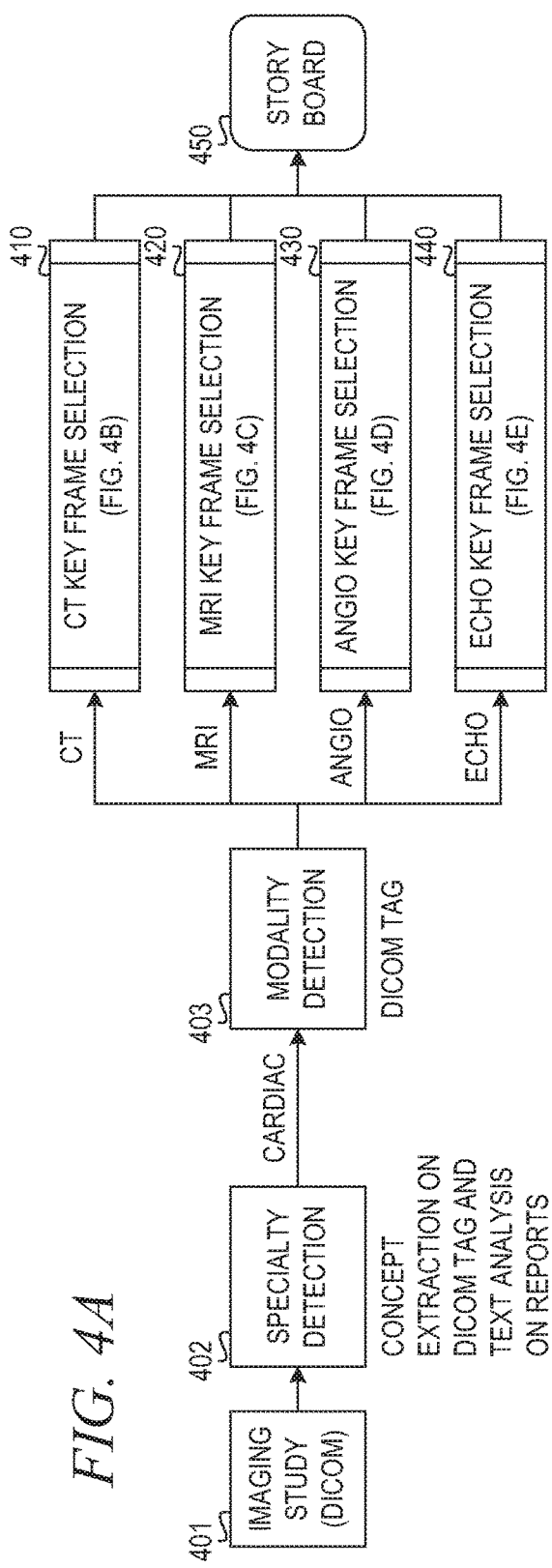
FIG. 4A is a block diagram illustrating an overall imaging story board creation engine pipeline in accordance with an illustrative embodiment.

FIG. 4A is a block diagram illustrating an overall imaging story board creation engine pipeline in accordance with an illustrative embodiment. Providing an image summary can optimize the workflow of a radiologist or cardiologist by bringing salient images to their attention by reducing the number of images that they have to study. FIG. 4A illustrates an overall pipeline for generating story boards based on the specialty of the physician and the modality of the imaging studies. The imaging story board creation engine pipeline includes a database, such as patient EMRs 322 in FIG. 3, to collect, search, and retrieve imaging studies of patients. This database can be a Picture Archiving and Communication System (PACS), Vendor Neutral Archive (VNA), or Analytics Longitudinal Patient Records (ALPR). Generally, any longitudinal patient record system that collects imaging and non-imaging patient data can be included. The system also includes algorithms to process images for story board generation and a database to record and retrieve the generated story board, such as EMRs 322 in FIG. 3. The image processing unit includes subsystems to detect image modality, image specialty, image view point, and salient images.

The story board is generated based on the image modality and the physician and study specialty. For example, a Radiologist may be looking at a Cardiac case. The system searches for the most recent studies of a patient, such as imaging study 401, which may be for a patient with cardiac disease, for example. Specialty detection component 402 investigates the retrieved imaging study 401 for detection of imaging study specialty. Specialty detection component 402 may examine Digital Imaging and Communications in Medicine (DICOM) tags such as study description, reason for study, body part scanned, or any other tag that can be used to detect the specialty. Digital Imaging and Communications in Medicine (DICOM) is a standard for storing and transmitting medical images enabling the integration of medical imaging devices such as scanners, servers, workstations, printers, network hardware, and picture archiving and communication systems (PACS) from multiple manufacturers. DICOM has been widely adopted by hospitals, and is making inroads into smaller applications like dentists' and doctors' offices. Alternatively, any corresponding report for that imaging study can be investigated to detect the study specialty. In another embodiment, the system may also look at previous text reports associated with the imaging study to find the specialty. Also, order information can be used.

If the study is not aligned with the target specialty, then the system may ignore the study. For example, for a patient with cardiac disease, only cardiac related imaging studies may be processed for inclusion in the story board 450.

Modality detection component 403 detects the modality of imaging study 401. The modality can be detected using DICOM tags or using image processing or machine learning algorithms if the DICOM tags are not available. Based on the detected mode, the imaging story board creation engine pipeline performs a sub-pipeline. Thus, if the detected modality is computerized tomography (CT), then CT key frame selection sub-pipeline 410 is executed, as discussed below with reference to FIG. 4B. If the detected modality is magnetic resonance imaging (MRI), then MRI key frame selection sub-pipeline 420 is executed, as discussed below with reference to FIG. 4C. If the detected modality is X-ray angiography, then the angiography key frame selection sub-pipeline 430 is executed, as discussed below with reference to FIG. 4D. If the detected modality is echocardiography, then the echocardiography key frame selection sub-pipeline 440 is executed, as discussed below with reference to FIG. 4E. Based on the result of the key frame selection sub-pipelines, the imaging story board creation engine generates story board 450 including the selected key frame images.

Figure 4B:
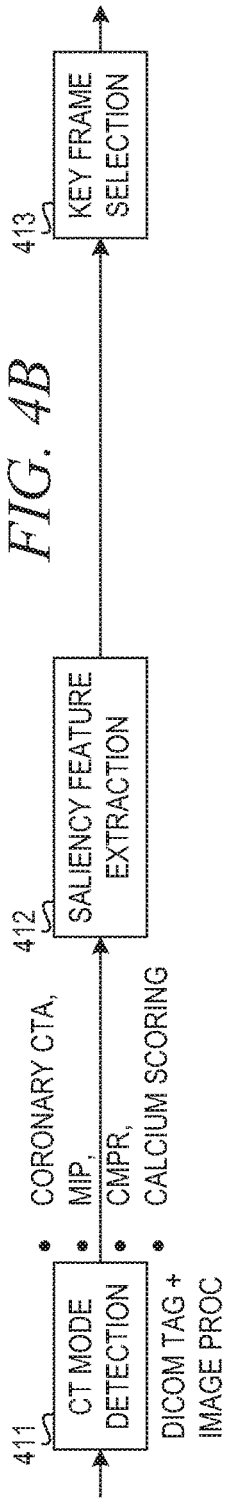
FIG. 4B is a block diagram illustrating a computerized tomography key frame selection sub-pipeline in accordance with an illustrative embodiment.

FIG. 4B is a block diagram illustrating a computerized tomography key frame selection sub-pipeline in accordance with an illustrative embodiment. Computerized Tomography (CT) mode detection component 411 executes a mode detection algorithm to detect the mode of images within the imaging study. For a CT imaging study, the mode may be, for example but not limited to, coronary computerized tomography angiogram (CTA), maximum intensity projection (MIP), curved multi-planar reconstruction (CMPR), or Calcium scoring. CT mode detection 411 may detect the imaging mode using text analysis on the DICOM tags, image processing algorithms, or machine learning methods, including deep learning.

Saliency feature extraction component 412 executes a saliency feature algorithm to identify salient features for images in the imaging study 401 based on the detected mode of the images by CT mode detector 411. All saliency features known in the art including topography variations can be used for selection. Key frame selection component 413 chooses images of a series of images to be added to story board 450. The images may be uniformly sampled to generate the story board 450. Alternatively, images in a series may be converted to a video clip and added to the story board 450.

Figure 4C:
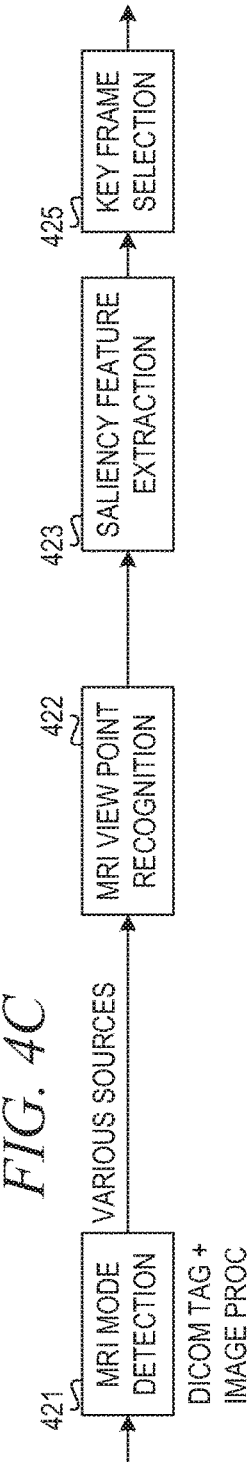
FIG. 4C is a block diagram illustrating a magnetic resonance imaging key frame selection sub-pipeline in accordance with an illustrative embodiment.

FIG. 4C is a block diagram illustrating a magnetic resonance imaging key frame selection sub-pipeline in accordance with an illustrative embodiment. Magnetic resonance imaging (MRI) mode detection component 421 executes a mode detection algorithm to detect the mode of images within the imaging study. For an MRI imaging study, different pulse sequences are the different modes. MRI mode detection component 421 may detect the imaging mode using text analysis on the DICOM tags, image processing algorithms, or machine learning methods, including deep learning.

MRI view point recognition component 422 recognizes the view point of images within the imaging study 401. Image processing algorithms can be used to detect the view point. Alternatively, machine learning methods, including deep learning, can be used to detect the view point.

Saliency feature extraction component 423 executes a saliency feature algorithm to identify salient features in the imaging study 401 based on the detected mode and view point of the imaging study 401. All saliency features known in the art including topography variations can be used for selection. Key frame selection component 425 chooses images of a series of images to be added to story board 450. The images may be uniformly sampled to generate the story board 450. Alternatively, images in a series may be converted to a video clip and added to the story board 450.

Figure 4D:
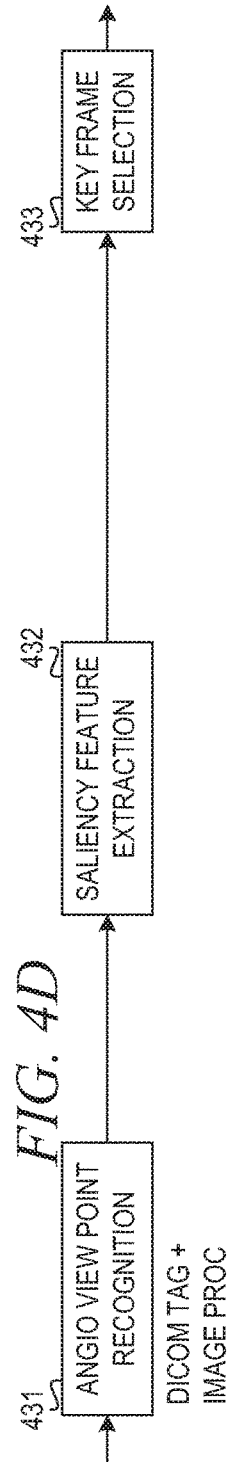
FIG. 4D is a block diagram illustrating an angiography key frame selection sub-pipeline in accordance with an illustrative embodiment.

FIG. 4D is a block diagram illustrating an angiography key frame selection sub-pipeline in accordance with an illustrative embodiment. Angiography view point recognition component 431 recognizes the view point of images within the imaging study 401. Image processing algorithms can be used to detect the view point. Alternatively, machine learning methods, including deep learning, can be used to detect the view point.

Saliency feature extraction component 432 executes a saliency feature algorithm to identify salient features for images in the imaging study 401 based on the detected view point of the imaging study 401. All saliency features known in the art including topography variations can be used for selection. Key frame selection component 433 chooses images of a series of images to be added to story board 450. The images may be uniformly sampled to generate the story board 450. Alternatively, images in a series may be converted to a video clip and added to the story board 450.

Figure 4E:
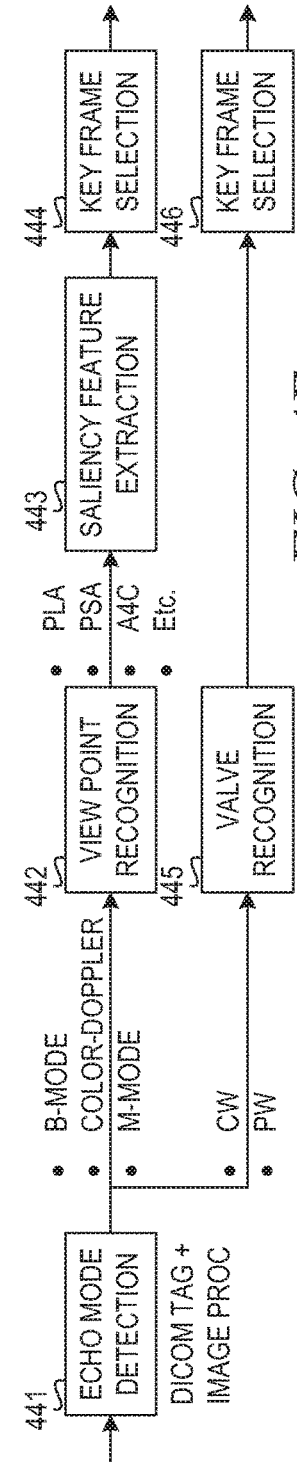
FIG. 4E is a block diagram illustrating an echocardiography key frame selection sub-pipeline in accordance with an illustrative embodiment.

FIG. 4E is a block diagram illustrating an echocardiography key frame selection sub-pipeline in accordance with an illustrative embodiment. Echocardiography mode detection component 441 executes a mode detection classifier to detect the echocardiography mode of images within the imaging study. For an echocardiography imaging study, the modes may include B-Mode, Color-Doppler, M-Mode, Continuous Wave (CW) Doppler, or Pulse Wave (PW) Doppler. Echocardiography mode detection component 441 may detect the imaging mode using text analysis on the DICOM tags, image processing algorithms, or machine learning methods, including deep learning. Specifically, the echocardiography mode detection is performed in this system using a convolution network (deep learning based classifier) if not available in the DICOM tags.

For B-Mode, Color-Doppler, and M-Mode imaging modes, view point recognition component 442 recognizes the view point of images within the imaging study 401. Image processing algorithms can be used to detect the view point. Alternatively, machine learning methods, including deep learning, can be used to detect the view point. The view point may be one of Parasternal long axis (PLA), Parasternal short axis (PSA), Apical 4-chambers (A4C), etc. (This list is not comprehensive. These are only examples.) Saliency feature extraction component 443 executes a saliency feature algorithm to identify salient features in the imaging study 401 based on the detected mode and view point of the imaging study 401. All saliency features known in the art can be used for selection. Key frame selection component 444 chooses images of a series of images to be added to story board 450. The images may be uniformly sampled to generate the story board 450. Alternatively, images in a series may be converted to a video clip and added to the story board 450.

For CW Doppler and PW Doppler imaging modes, valve recognition component 445 executes algorithms for recognizing the valve shown in images within the imaging study 401. Image processing algorithms can be used to detect the valve. Alternatively, machine learning methods, including deep learning, can be used. Key frame selection component 446 chooses images of a series of images to be added to story board 450. The images may be uniformly sampled to generate the story board 450. M-Mode, CW, and PW images are single images that can go to the storyboard directly. Saliency detection and key frame selection are for multi-frame/slice images. Alternatively, images in a series may be converted to a video clip and added to the story board 450.

Returning to FIG. 4A, the imaging story board creation engine saves the story board 450 in the database, such as EMRs 322 in FIG. 3, to be retrieved later and presented to the clinician.

Figure 5B:
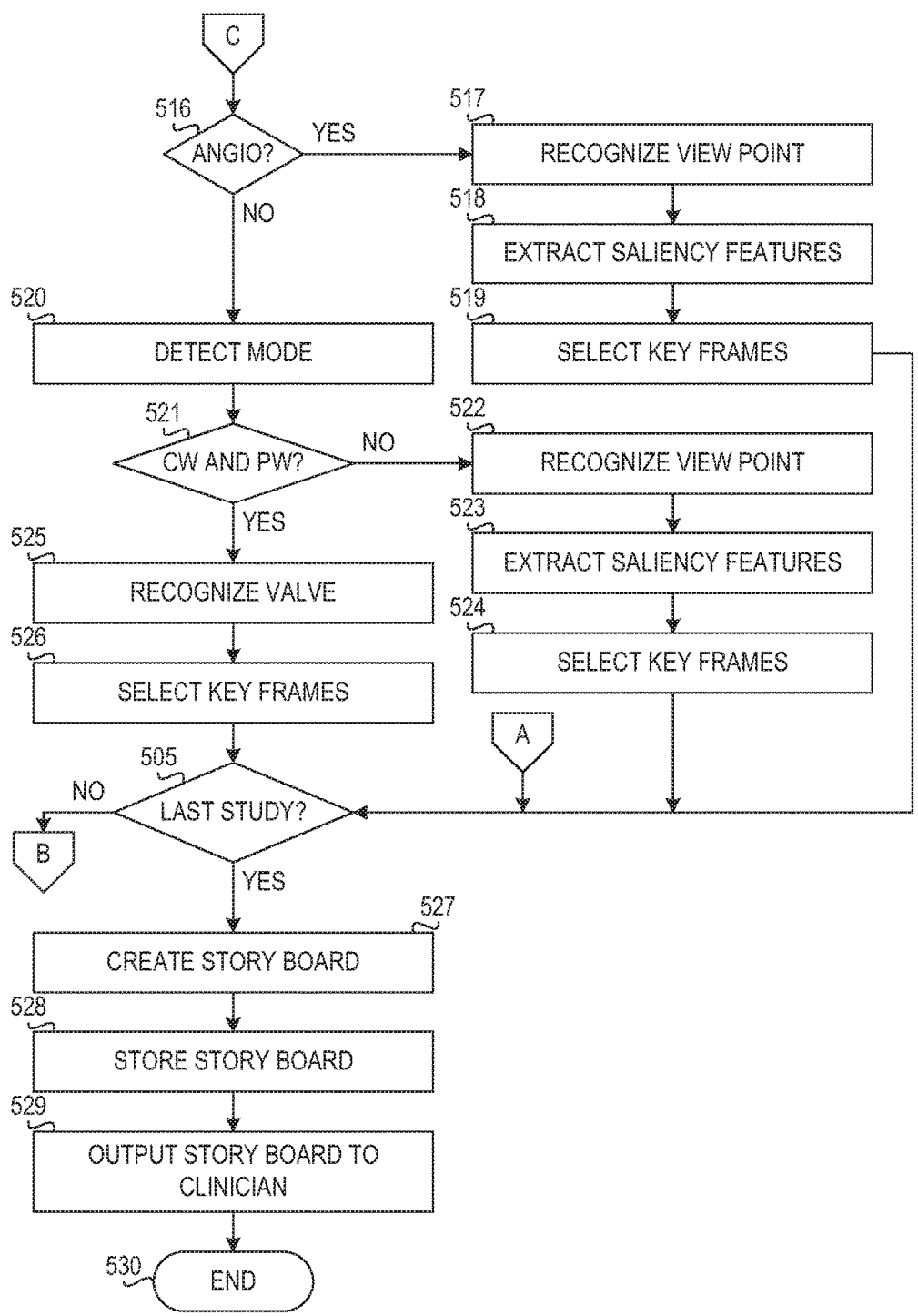

FIGS. 5A and 5B present a flowchart of a mechanism for automatic creation of imaging story boards from medical imaging studies in accordance with an illustrative embodiment. With reference to FIG. 5A, operation begins (block 500), and the mechanism searches for the most recent imaging studies of the patient (block 501). The mechanism investigates the imaging studies for detection of the imaging study specialty (block 502). DICOM tags such as study description, reason for study, body part scanned, or any other tag can be investigated to detect the specialty. Any corresponding report for that imaging study can be investigated to detect the specialty, such as via natural language processing, metadata analysis, or the like.

The mechanism then determines whether the imaging study specialty is aligned with the target specialty for which the patient is being examined (block 503). If the imaging study specialty is not aligned with the target specialty, i.e., does not have the same or a related specialty to that of the required specialty for the story board generation (e.g., the specialty of the physician for which the story board is being generated or a specified specialty associated with the story board indicating a reason or subject matter of the story board), then the mechanism ignores the study (block 504), and operation proceeds to block 505 in FIG. 5B. For example, for a patient with cardiac disease, whose imaging studies will be viewed by a cardiac specialist, only cardiac related imaging studies are processed. The mechanism then determines whether the imaging study is the last imaging study to be considered for the medical imaging story board (block 505). If the imaging study is not the last study to be considered, then operation returns to block 502 in FIG. 5A to investigate the next imaging study.

If the imaging study specialty is aligned with the target specialty in block 503, then the mechanism detects the modality of the imaging study (block 506). The mechanism determines whether the modality is computerized tomography (CT) (block 507). If the modality is CT, then the mechanism detects the mode of images within the imaging study (block 508). As discussed above with reference to FIG. 4B, a CT mode detection component performs text analysis on the DICOM tags for mode detection. Alternatively, image processing algorithms can be used to detect the mode. In one embodiment, machine learning methods, including deep learning, can be used to detect the mode. Then, the mechanism extracts saliency features (block 509). All saliency features known in the art, including topography variations or disease/abnormality based features, can be used. The mechanism then selects key frames to be included in the story board based on the detected mode and saliency features (block 510). Thereafter, operation returns to block 505 to determine whether the imaging study is the last imaging study to be considered.

If the modality is not CT in block 507 then the mechanism determines whether the modality is magnetic resonance imaging (MRI) (block 511). If the modality is MRI, then the mechanism detects the mode of images within the imaging study (block 512). As discussed above with reference to FIG. 4C, MRI mode detection component 421 may detect the imaging mode using text analysis on the DICOM tags, image processing algorithms, or machine learning methods, including deep learning. For an MRI imaging study, different pulse sequences are the different modes. The mechanism then recognizes the view point of images within the imaging study (block 513). As discussed above with reference to FIG. 4C, MRI view point recognition component 422 recognizes the view point of the images. Image processing algorithms can be used to detect the view point. Alternatively, machine learning methods, including deep learning, can be used to detect the view point. The mechanism then extracts saliency features (block 514) and selects key frames based on the detected mode, the view point, and the extracted saliency features (block 515). Thereafter, operation proceeds to block 505 to determine whether the imaging study is the last imaging study to be considered.

If the modality is not MRI in block 511, then operation proceeds to block 516 to determine whether the modality is angiography. If the modality is angiography, then the mechanism recognizes the mode of images within the imaging study (block 517), extracts the saliency features (block 518), and selects key frames (block 519). As discussed above with reference to FIG. 4D, angiography view point recognition component 431 recognizes the view point of the imaging study using image processing algorithms or machine learning methods, including deep learning. Thereafter, operation proceeds to block 505 to determine whether the imaging study is the last imaging study to be considered.

If the modality is not angiography in block 516, then the modality is echocardiography, and the mechanism detects the mode of images within the imaging study (block 520). As discussed above with reference to FIG. 4E, echocardiography mode detection component 441 may execute a mode detection deep learning classifier to detect the echocardiography mode of the imaging study. Specifically, the echocardiography mode detection is performed in this system using a convolution network (deep learning based classifier) if not available in the DICOM tags. The mechanism then determines whether the mode is Continuous Wave (CW) Doppler or Pulse Wave (PW) Doppler (block 521). If the mode is not CW Doppler or PW Doppler, then the mechanism recognizes the view point (block 522), extracts saliency features (block 523), and selects key frames (block 524). As discussed above with reference to FIG. 4E, for B-Mode, Color-Doppler, and M-Mode imaging modes, view point recognition component 442 recognizes the view point of images within the imaging study using image processing algorithms or machine learning methods, including deep learning. Thereafter, operation proceeds to block 505 to determine whether the imaging study is the last imaging study to be considered.

If the mode is CW Doppler or PW Doppler in block 521, then the mechanism recognizes the valve in the images of the imaging study (block 525). Image processing algorithms can be used to detect the valve. Alternatively, machine learning methods, including deep learning, can be used. Then, the mechanism selects key frames (block 526). Thereafter, operation proceeds to block 505 to determine whether the imaging study is the last imaging study to be considered.

If the imaging study is the last study to be considered for inclusion in the story board in block 505, then the mechanism generates the story board (block 527), stores the story board (block 528), and outputs the story board to the clinician (block 529). Thereafter, operation ends (block 530).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a medical imaging story board creation engine, the method comprising:
   receiving, by the medical imaging story board creation engine executing in the data processing system, a patient data structure comprising a medical imaging study comprising a plurality of electronic medical images;
   analyzing, by a modality detection component executing within the medical imaging story board creation engine, the patient data structure to determine a modality of the medical imaging study;
   determining, by the medical imaging story board creation engine, based on the determined modality of the medical imaging study, for each electronic image in the medical imaging study, at least one of an imaging mode or viewpoint;
   performing, by a saliency feature extraction component executing within the medical imaging story board creation engine, a saliency feature extraction operation on the electronic medical images in the medical imaging study based on the image mode or viewpoint of each of the electronic medical images;
   selecting, by a key frame selection component executing within the medical imaging story board creation engine, a subset of electronic medical images based on results of the saliency feature extraction; and
   generating and outputting, by the medical imaging story board creation engine, a collection of selected electronic medical images based on the selection of the subset of electronic medical images to form a medical imaging story board.

2. The method of claim 1, further comprising:
   determining, by a specialty detection component executing within the medical imaging story board creation engine, a first specialty attribute associated with a collection of electronic medical images to be generated;
   determining, by the specialty detection component, for each medical imaging study data structure present in the patient data structure, a corresponding second specialty attribute associated with medical imaging study data structure; and
   eliminating, by the specialty detection component, medical imaging study data structures present in the patient data structure that have a second specialty attribute that does not match the first specialty attribute from further processing to generate the collection of selected electronic medical images.

3. The method of claim 2, wherein the specialty detection component examines Digital Imaging and Communications in Medicine (DICOM) tags to determine the second specialty attribute.

4. The method of claim 3, wherein DICOM tags comprise at least one of study description, reason for study, or body part scanned.

5. The method of claim 1, wherein generating and outputting the collection of selected electronic medical images comprises generating a storyboard data structure and outputting, via a graphical user interface, a visualization of the storyboard data structure, and wherein the storyboard data structure comprises electronic medical images of different modalities, different modes, or different viewpoints.

6. The method of claim 1, wherein determining an imaging mode comprises determines the imaging mode using text analysis on the DICOM tags, image processing algorithms, or machine learning methods.

7. The method of claim 1, wherein determining a view point comprises recognizing the view point of images within the imaging study using image processing algorithms or machine learning methods.

8. The method of claim 1, further comprising:
responsive to the modality detection component determining the modality of the medical imaging study is computerized tomography (CT), determining, by a CT mode detection component executing within the medical imaging story board creation engine, an imaging mode of images within the medical imaging study,
wherein the saliency feature extraction component performs the saliency feature extraction operation on the electronic medical images in the medical imaging study based on the determined image mode.

9. The method of claim 8, wherein the determined image modes comprise one or more of coronary computerized tomography angiogram (CTA), maximum intensity projection (MIP), curved multi-planar reconstruction (CMPR), or Calcium scoring.

10. The method of claim 1, further comprising:
responsive to the modality detection component determining the modality of the medical imaging study is magnetic resonance imaging (MRI), determining, by an MRI mode detection component executing within the medical imaging story board creation engine, an imaging mode of images within the medical imaging study; and
determining, by an MRI view point recognition component executing within the medical imaging story board creation engine, a viewpoint of the images within the medical imaging study,
wherein the saliency feature extraction component performs the saliency feature extraction operation on the electronic medical images in the medical imaging study based on the determined image mode and the determined view point.

11. The method of claim 10, wherein the determined image modes comprise one or more pulse sequences.

12. The method of claim 1, further comprising:
responsive to the modality detection component determining the modality of the medical imaging study is angiography, determining, by an angiography view point recognition component executing within the medical imaging story board creation engine, a viewpoint of the images within the medical imaging study,
wherein the saliency feature extraction component performs the saliency feature extraction operation on the electronic medical images in the medical imaging study based on the determined image mode and the determined view point.

13. The method of claim 1, further comprising:
responsive to the modality detection component determining the modality of the medical imaging study is echocardiography B-Mode, Color-Doppler, or M-Mode imaging mode, determining, by an echocardiography view point recognition component executing within the medical imaging story board creation engine, a viewpoint of images within the medical imaging study,
wherein the saliency feature extraction component performs the saliency feature extraction operation on the electronic medical images in the medical imaging study based on the determined image mode and the determined view point.

14. The method of claim 1, further comprising:
responsive to the modality detection component determining the modality of the medical imaging study is echocardiography CW Doppler or PW Doppler imaging modes imaging mode, recognizing, by a valve recognition component executing within the medical imaging story board creation engine, a valve shown in images within the medical imaging study.

15. The method of claim 14, wherein the valve recognition component uses image processing algorithms or machine learning methods.

16. A computer program product comprising a computer readable storage medium having a computer readable program stored therein, wherein the computer readable program, when executed on at least one processor of a data processing system, causes the data processing system to implement a medical imaging story board creation engine, wherein the computer readable program causes the data processing system to:
receive, by the medical imaging story board creation engine executing in the data processing system, a patient data structure comprising a medical imaging study comprising a plurality of electronic medical images;
analyze, by a modality detection component executing within the medical imaging story board creation engine, the patient data structure to determine a modality of the medical imaging study;
determine, by the medical imaging story board creation engine, based on the determined modality of the medical imaging study, for each electronic image in the medical imaging study, at least one of an imaging mode or viewpoint;
perform, by a saliency feature extraction component executing within the medical imaging story board creation engine, a saliency feature extraction operation on the electronic medical images in the medical imaging study based on the image mode or viewpoint of each of the electronic medical images;
select, by a key frame selection component executing within the medical imaging story board creation engine, a subset of electronic medical images based on results of the saliency feature extraction; and
generate and output, by the medical imaging story board creation engine, a collection of selected electronic medical images based on the selection of the subset of electronic medical images to form a medical imaging story board.

17. The computer program product of claim 16, wherein the computer readable program further causes the data processing system to:
determining, by a specialty detection component executing within the medical imaging story board creation engine, a first specialty attribute associated with a collection of electronic medical images to be generated;
determining, by the specialty detection component, for each medical imaging study data structure present in the patient data structure, a corresponding second specialty attribute associated with medical imaging study data structure; and
eliminating, by the specialty detection component, medical imaging study data structures present in the patient data structure that have a second specialty attribute that does not match the first specialty attribute from further processing to generate the collection of selected electronic medical images.

18. The computer program product of claim 16, wherein generating and outputting the collection of selected electronic medical images comprises generating a storyboard data structure and outputting, via a graphical user interface, a visualization of the storyboard data structure, and wherein the storyboard data structure comprises electronic medical images of different modalities, different modes, or different viewpoints.

19. An apparatus comprising:
a processor; and
a memory coupled to the processor, wherein the memory comprises instructions which, when executed by the processor, cause the processor to implement a medical imaging story board creation engine, wherein the instructions cause the processor to:
receive, by the medical imaging story board creation engine executing in the data processing system, a patient data structure comprising a medical imaging study comprising a plurality of electronic medical images;
analyze, by a modality detection component executing within the medical imaging story board creation engine, the patient data structure to determine a modality of the medical imaging study;
determine, by the medical imaging story board creation engine, based on the determined modality of the medical imaging study, for each electronic image in the medical imaging study, at least one of an imaging mode or viewpoint;
perform, by a saliency feature extraction component executing within the medical imaging story board creation engine, a saliency feature extraction operation on the electronic medical images in the medical imaging study based on the image mode or viewpoint of each of the electronic medical images;
select, by a key frame selection component executing within the medical imaging story board creation engine, a subset of electronic medical images based on results of the saliency feature extraction; and
generate and output, by the medical imaging story board creation engine, a collection of selected electronic medical images based on the selection of the subset of electronic medical images to form a medical imaging story board.

20. The apparatus of claim 19, wherein the instructions further cause the processor to:
determine, by a specialty detection component executing within the medical imaging story board creation engine, a first specialty attribute associated with a collection of electronic medical images to be generated;
determine, by the specialty detection component, for each medical imaging study data structure present in the patient data structure, a corresponding second specialty attribute associated with medical imaging study data structure; and
eliminate, by the specialty detection component, medical imaging study data structures present in the patient data structure that have a second specialty attribute that does not match the first specialty attribute from further processing to generate the collection of selected electronic medical images.

* * * * *